(12) United States Patent
Zhu et al.

(10) Patent No.: US 6,517,554 B1
(45) Date of Patent: Feb. 11, 2003

(54) EVERTING TRICEPS

(76) Inventors: Yong Hua Zhu, 30919 Sutherland Dr., Redlands, CA (US) 92373; Wolff M. Kirsch, 1360 Prospect Dr., Redlands, CA (US) 92373

(*) Notice: Subject to any disclaimer, the term of this patent is extended or adjusted under 35 U.S.C. 154(b) by 0 days.

(21) Appl. No.: 09/620,621

(22) Filed: Jul. 20, 2000

Related U.S. Application Data (60) Provisional application No. 60/144,763, filed on Jul. 20, 1999.

(51) Int. Cl.[7] ............................................. A61B 17/04
(52) U.S. Cl. ........................ 606/150; 606/205; 606/210
(58) Field of Search ................................ 606/205–207, 606/150

(56) References Cited

U.S. PATENT DOCUMENTS

| | | | |
|---|---|---|---|
| 4,800,880 A | * | 1/1989 | Catalano ..................... 606/205 |
| 4,950,281 A | * | 8/1990 | Kirsch et al. ................ 606/207 |
| 5,520,704 A | * | 5/1996 | Castro et al. ................ 606/208 |

* cited by examiner

*Primary Examiner*—Gary Jackson
(74) *Attorney, Agent, or Firm*—Knobbe, Martens, Olson & Bear, LLP (57) ABSTRACT

A triceps for anastomosis, the triceps having two outer legs on opposing sides of a middle leg. A latch is located on one outer leg and the middle leg to hold the respective legs in a clamped position. An alignment post extends through the middle leg and cooperates with holes in the outer legs to allow the post to enter the holes and ensure alignment of the legs in use. The post has an enlarged base portion that does not pass through the hole and thereby limits movement of the outer legs relative to the inner legs and thereby limits clamping pressure at the free ends of the legs. The free ends of the legs have various cooperating shapes to facilitate everting and aligning tubular vessels and body tissue for anastomosis.

16 Claims, 3 Drawing Sheets

EVERTING TRICEPS

RELATED APPLICATIONS

This application claims the benefit of U.S. Provisional Application No. 60/144,763, filed Jul. 20, 1999, titled EVERTING TRICEPS, the entirety of which is hereby incorporated by reference.

FIELD OF THE INVENTION

This invention relates to surgical devices, and in particular to a triceps or everting forceps for performing anastomosis that include skin closures and tissue closures.

BACKGROUND OF THE INVENTION

As used herein, an anastomosis refers to a variety of procedures in which blood vessels, other tubular body parts, or body tissue are surgically joined or reconnected using clips, sutures, adhesives, etc. The joinder is not limited to tubular structures, and may include solid body parts such as skin, nerves or other body tissue. The tubular vessels and tissue may be joined end-to-end or end-to-side. For ease of reference, the discussion will primarily refer to joining tubular vessels.

Anastomosis typically involves mechanically joining vessels, typically using clips, sutures, etc. To do so, the edges of the vessel are first everted, or turned outward to form flanges that may be gripped by the clips or fastening mechanism. Eversion increases the ease and reliability of the mechanical joining, and places the interior surfaces of the vessels in contact. For non-penetrating joinder, as used in some surgical clips, it is preferred that the eversion be accurate and symmetric with the edges of the tissue aligned to facilitate fastening. But symmetric eversion is difficult to achieve and maintain while applying the clips. Thus, there is a need for an improved tool to align the edges of the vessels and other body parts for joining by anastomosis.

Furthermore, while performing anastomosis, the surgeon must often use one side a triceps tool to grip and position one vessel or piece of tissue, and use the other side of the triceps to grip and position the other vessel or piece of tissue to be joined. It can be difficult to hold two vessels or pieces of tissue with one instrument. In addition, to achieve the proper grip the surgeon must squeeze the triceps with the correct amount of pressure. If squeezed too tightly the triceps may damage the tissue either by pinching crushing, or more often because the triceps tips slide over each other and create a scissoring action that can cut the tissue. If squeezed too loosely, the tissue is difficult to position or even falls out of the triceps. The requirement of a precise triceps holding pressure is complicated by the need to hold two vessels or pieces of tissue simultaneously. There is thus a need for a way to adequately grip the body parts without damaging them, and to manipulate those parts into position for anastomosis.

Moreover, it is advantageous that the same surgeon both positions the body parts for anastomosis and performs the joinder of the vessels/tissues, by placing surgical clips or otherwise. Thus, it is advantageous that the surgeon handle the triceps with one hand while performing the joinder with the other. Accordingly, there is a need for a hand operable tool that permits the same surgeon to both hold the body parts for anastomosis and apply the surgical clips or other means for joining the body parts.

SUMMARY OF THE INVENTION

The triceps of this invention allows compression of two outer legs toward each other and toward a middle leg so a surgeon can engage tissue for anastomosis between the distal ends of the middle leg and one or both of the outer legs. By removably latching at least one of the outer legs relative to the middle leg, and latching in a position to hold the engaged tissue without damage, the surgeon can better manipulate the triceps. The latch mechanism essentially relieves the surgeon of applying the correct pressure and avoids accidentally disengaging the tissue from the latched portion of the triceps. Advantageously, the latching is achieved by moving at least one of the middle and the outer legs toward each other to latch, with further movement toward each other disengaging the latch mechanism. A Castro Viejho latching mechanism is preferred.

A further advantage is offered by interposing a stop intermediate the middle leg and one or both of the outer legs to limit the motion of the distal ends of the outer legs and to prevent gripping the body tissue too tightly. However, the grip on the engaged tissue can also be loosened, or even tightened, despite the stop. For example, if the stop engages a first outer leg, then by pressing on that first outer leg between the stop and the distal end the grip on the body tissue can be tightened. But pressing on that outer leg between the joined ends and the stop will cause the outer leg to pivot about the stop and open the distal ends, thus loosening the grip on the tissue and allowing adjustments. By placing a finger on each opposing side of the stop, the surgeon can pivot the outer leg and its distal end to open or close one side of the triceps. This allows fine adjustments in the gripping force to facilitate manipulation of gripped tissue.

A similar advantage arises by interposing a stop intermediate the latch mechanism and the distal end of the outer leg. The middle and outer legs can be moved toward each other until either the stop or the latch limits the motion. Advantageously, the relative motion is stopped at a point where the distal end of the middle and outer leg grip the tissue firmly enough to position it for anastomosis without damaging the tissue. The latching mechanism is then engaged to hold the engaged tissue. But the grip on that engaged tissue can be adjusted by pressing between the latch mechanism and the stop, which causes the outer leg to pivot about the stop and loosen the grip on the engaged tissue. By placing a finger on each opposing side of the stop, the surgeon can pivot the outer leg and its distal end to open or close one side of the triceps. There is provided a means of holding the tissue with a triceps while adjusting the grip on the body tissue to facilitate repositioning and manipulating the triceps or tissue.

Additionally, the distal end of the middle leg preferably has a convexly curved surface, and is preferably circular or elliptical with the major axis of the ellipse intersecting the distal ends of the outer legs of the triceps. The distal ends of the adjoining outer legs have concavely curved surfaces that are advantageously, but not necessarily, of a different radius of curvature than the convex surface. When the concave distal ends of the outer legs urge tissue against the convex surface of the middle leg, the tissue everts. The different shapes of the distal ends of the legs help the eversion, with the curvature being gradual enough to avoid cutting or damaging the engaged tissue. There is thus provided an advantageous shape of the distal ends to evert the tissue for anastomosis. Further, by urging the everted tissue against the flange, the aligned tissue is more easily joined.

There is provided a surgical triceps having three legs fastened at one end, and including two outer legs on opposing sides of a middle leg, the outer legs being configured to be separated from the middle leg and resiliently urgable toward the middle leg by finger pressure. Each leg has a free distal end that is separated from the adjacent distal ends but which may be resiliently urged together by finger pressure. The distal ends are configured for anastomosis so that in use, first and second pieces of tissue can be urged by the distal ends of the outer legs against the distal end of the middle leg with sufficient force to hold the tissue for joining. Preferably a Castro Viejho latch is placed on at least one of the legs engaging a portion of an adjacent leg to hold the adjacent legs in position. The latch is configured to achieve a predetermined spacing at the distal ends of the adjacent legs such that the distal end of the one outer leg and the distal end of the middle leg are spaced apart a distance sufficient to hold tissue for anastomosis.

Further, an alignment member advantageously extends from one of the middle or one of the outer legs and is aligned to engage a recess in the other of the middle or the other of the outer legs to ensure alignment of the distal ends of the middle leg and an adjacent distal end on one of the legs when the member engages the recess. Moreover, a stop preferably extends from one of the legs and is oriented so that the stop is interposed between two adjacent legs to contact and limit motion between said adjacent legs upon contact. Preferably, the stop and alignment member are coaxially located on a common member.

A feature is also provided for symmetric eversion. The distal end of the middle leg can have a flange extending outwardly from it, the flange being spaced from the distal end and toward the fastened ends a distance sufficient to contact the tissue being gripped by adjacent legs to align the tissue for symmetric eversion during use of the triceps. The flange extends from the middle leg a distance adequate to block passage of tissue to be joined by anastomosis during use of the triceps.

As described briefly above, and in more detail below, there is thus provided a latching means for holding at least two of the legs in a predetermined position relative to each other to hold body tissue in the distal ends of at least two legs. Further, the triceps can have alignment means for aligning the middle leg and at least one of the outer legs as the distal end of the aligned outer leg urges body tissue toward the distal end of the middle leg when in use. Moreover, the triceps can have means for limiting motion of the middle leg relative to one of the outer legs. Finally, the triceps can have means on the distal ends of the legs for everting tubular vessels, and aligning them for symmetric eversion.

The present invention also includes a new method for anastomosis using finger operated triceps having three legs fastened at one end and having distal ends configured for anastomosis. The method includes the step of manually moving the first leg toward the middle leg and engaging tissue for anastomosis between the distal ends of the middle leg and the first leg. The first outer leg and middle leg are removably latched in a position to hold the engaged tissue. As needed, the method engages a stop interposed between the first and middle legs to limit the relative motion between the distal ends of the first and middle legs. In further variations, the method also includes manually moving the second leg toward the middle leg and engaging tissue for anastomosis between the distal ends of the middle leg and the second leg. Additionally, the surgeon can urge an end of the tissue engaged between the first and middle legs and between the second and middle legs against an outwardly extending flange on the middle leg to align the ends of the tissue with the flange for symmetric eversion. As desired, the surgeon can also engage a stop interposed between the second and middle legs to limit the relative motion between the distal ends of the second and middle legs to prevent tissue damage from the triceps. Moreover, by interposing the stop intermediate the middle and first outer legs and between the latch and the distal end of the first outer leg, the surgeon can move the middle and first outer legs toward each other until the stop limits the motion of the middle and first outer legs, and yet still be able to open the distance between the distal ends of the middle and first outer legs by pressing on the first outer leg intermediate the stop and the latch.

BRIEF DESCRIPTION OF THE DRAWINGS

These and other advantages and objects of the invention will be better understood by reference to the following drawings in which like numbers refer to like parts throughout.

DETAILED DESCRIPTION OF THE PREFERRED EMBODIMENT

Figure 1:
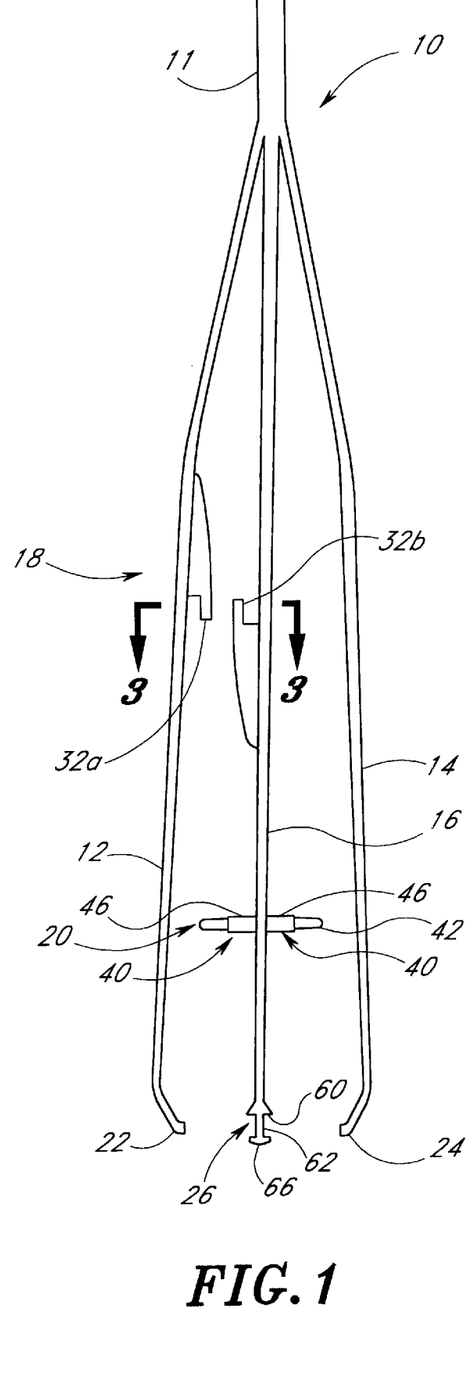
FIG. 1 is a front plan view of the triceps of this invention.
Figure 2:
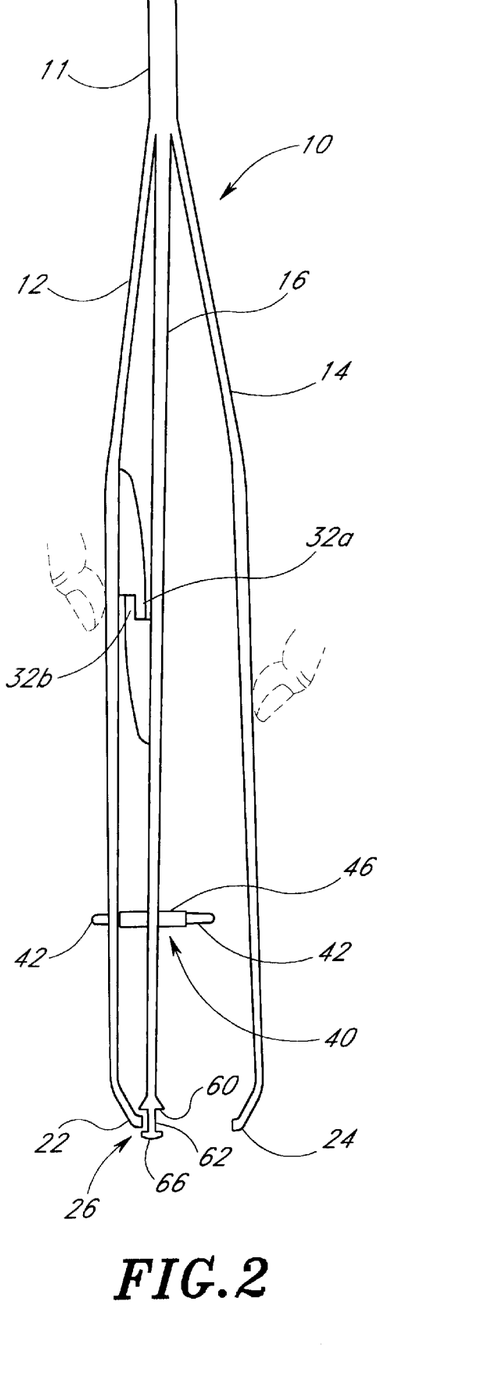
FIG. 2 is a front plan view of the triceps of FIG. 1 with one outer leg in a latched and aligned position.

Referring to FIGS. 1 and 2, a triceps 10 is provided for anastomosis. The triceps 10 has three legs, two outer legs 12, 14 on opposing sides of middle leg 16. The legs 12, 14, 16 each have a longitudinal axis and advantageously these longitudinal axes are co-planar. The legs 12, 14 and 16 each have a free, distal end and an opposing, joined end 11 that is permanently joined to the other legs, preferably by laminating and welding, soldering or gluing the joined ends. Other joining mechanisms can be used depending on the materials.

A latch mechanism 18 is located intermediate the joined and distal ends of the legs. An alignment and motion limiting mechanism 20 is also located on the legs, advantageously intermediate the latch mechanism 18 and the distal ends of the legs. The distal ends 22, 24, 26 of the legs 12, 14, 16, respectively, have ends shaped to facilitate anastomosis, as described later. While the legs 12, 14 and 16 are joined at one end 11, the outer legs 12, 14 are bent so that they extend away from the straight middle leg 16 and then are bent again so they are generally parallel to the middle leg 16. This results in the distal ends 22, 24 of outer legs 12, 14 being separated from the distal end 26 of the middle leg. The legs 12, 14 are resilient and can be resiliently urged toward the middle leg 16 by a squeezing action applied by the surgeon's fingers to the outer legs 12, 14. As shown in FIGS. 1 and 2, distal ends 22 and 24 are preferably bent slightly toward middle end 26.

Figure 3:
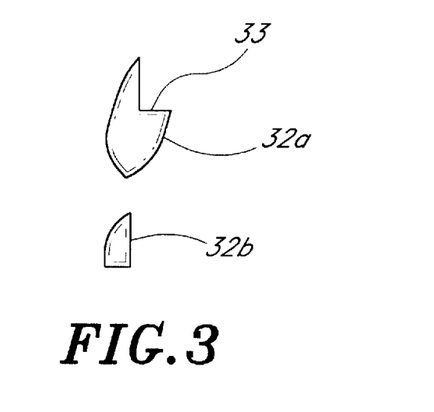
FIG. 3 is a side view of a latching mechanism of the triceps of FIG. 1 taken along section 3—3.

Referring to FIGS. 1–3, the latching mechanism 18 will be described. The mechanism 18 comprises latch members 32a, 32b, one on each of two adjacent and opposing legs, shown in the figures as outer leg 12 and middle leg 16. Each latch member 32a, 32b is generally aligned with the longitudinal axis of the leg to which it is fastened, but offset from that leg by a distance that is greater than the thickness of the latch member 32. The latch members 32a, 32b are aligned in opposing directions. The latch members 32 are permanently fastened to the legs 12, 16 by welding, brazing, soldering, by integrally molding the latch members 32 with the legs, or other means now known or discovered in the future.

The latch mechanism 18 is preferably of the type known in the art, by which members are releasably engaged by squeezing opposing sides of said members. These are commonly called Castro Viejho locks, although other latching mechanisms could be used that are manually engaged and disengaged by one hand. Briefly described, the lock has a latch member 32a on the outer leg 12 with a cross-sectional shape that resembles an ellipse with the apex directed toward the middle leg 16. A notch comprising about a quarter section of the ellipse is cut out of the cross-section adjacent the outer leg 12 to form a latching surface 33. The opposing latching member 32b has a cross-section resembling a quarter circle or a triangular shape, with the narrow end of the cross-section directed toward the latch member 32a. The apex or point of each latch member 32a, 32b are aligned so that they cause the members 32a, 32b to abut but slide past each other on the inclined surfaces so that the base of the member 32b engages the notched latching surface 33 of member 32a to latch the middle leg 16 to outer leg 12. Thus, the axis through the centers of each of the latching members 32a, 32b is slightly offset. In the latched position the inclined surfaces of abutting members 32a, 32b cause the members 32a, 32b to move laterally relative to each other so the members 32a, 32b are resiliently urged together.

Urging the legs 12, 16 further toward each other causes the base of the member 32b to pass over the end of the notched latching surface 33 and resiliently move toward the side of the latch member 32a opposite the latching surface 33, so that when released, the members 32a, 32b do not engage. Thus, pushing the latching members 32a, 32b toward each other a first distance engages the latch members 32a, 32b and latches the legs 12, 14 in position relative to each other, but moving the latches members 32a, 32b further toward each other disengages the latch members and frees the legs 12, 14. Other latches can be used, including latches commonly used with forceps that require slight lateral movement of the legs 12, 14 relative to each other in order to disengage the latch members.

Advantageously, the latch mechanism 18 prevents the outer leg 12 from moving away from the middle leg 16. Further, the latch mechanism 18 preferably allows some movement of the outer leg 12 toward the middle leg 16 before engagement of the latching mechanism. Additionally, once engaged, the latch mechanism 18 preferably allows little movement of the outer leg 12 toward the middle leg 18 at the location of the latch mechanism 18. Given the above and following disclosure, other latch mechanisms can be used to achieve these separate and/or combined functions. The latch members 32 are advantageously located about ⅓ the length of the outer legs 12, 16 away from the joined end 11 of the legs. Other locations along the length of the triceps can be used as desired.

While the embodiment of FIGS. 1–3 shows a single latching mechanism 18, the cooperative parts of a latching mechanism 18 could also be placed on middle leg 16 and outer leg 14. Thus, the triceps 10 preferably contains at least one latching mechanism 18, but could contain two such latching mechanisms. The latch mechanism 18 engages a portion of another leg to hold the engaged legs in a predetermined position. Advantageously the latch mechanism 18 is located on the legs 12, 14, 16, and configured to achieve a predetermined spacing at the distal ends 22, 24, 26 of the legs such that the distal end 22 or 24 of the engaged outer leg 12 or 14, and the distal end 26 of the middle leg 16, are spaced apart a distance sufficient to hold a vessel wall or other tissue for joining.

Figure 4:
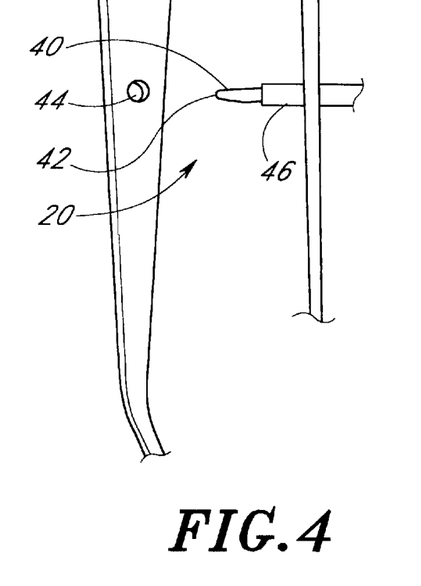
FIG. 4 is an exploded view of an alignment and motion limiting mechanism of the triceps of FIG. 1.

Referring to FIGS. 1, 2 and 4, the alignment and motion limiting mechanism 20 is located toward the distal end of the triceps 10. The alignment portion of the mechanism 20 comprises a member extending from one leg toward an adjacent leg cooperating with a recess, which can include a hole or aperture on the adjacent leg to align movement of the legs. Advantageously, the member comprises an elongated member, such as a post 40 extending laterally from the middle leg 16 toward the outer leg 12. An identical post 40 is located on the opposing side of the middle leg 16 and extends toward the outer leg 14. Each of the posts 40 preferably has a tapered end 42 which is aligned with a recess in the adjacent outer leg 12 or 14. Advantageously the recess comprises an aperture or hole 44 (FIG. 4) in the corresponding outer leg 12, 14. The tapered end 42 of post 40 is smaller than the hole 44 and enters the hole 44 to guide the end 42 into further engagement with the hole 44. Advantageously, the hole 44 is circular.

The post 40 is fastened to the leg 16 by means suitable for providing a strong connection. If of plastic, the post 40 may be ultrasonically welded, glued, or integrally molded with the leg 16. If of metal, the post 40 is advantageously soldered, brazed or welded to the leg 16, although preferably the post 40 is press fit through a hole in the leg 16 so that it extends from both sides of the middle leg 16. Alternatively, the post 40 could extend from one or both of the outer legs 12, 14 toward a recess 44 located in the middle leg 16. The post 40 and its end 42 are sized to resist lateral movement of the middle leg 16 relative to the outer legs 12 and/or 14 that are engaged by a post 40 and thus ensure alignment of the longitudinal axes of the legs 12, 14 and 16. The engagement of the end 42 with the hole 44 thus provides a means to maintain alignment of the legs engaged by post 40. More importantly, it also aligns the distal ends 22, 24, 26 of the legs so the ends do not slide past each other in a scissors action to cut the engaged tissue.

The motion limiting portion of mechanism 20 comprises a stop which is placed on an adjacent leg to limit motion of two adjacent legs toward each other. This helps prevent crushing the tissue engaged by the distal ends 22, 24, 26, and if additional pressure is applied it actually opens the triceps by increasing the distance of the ends 22, 24, 26.

Advantageously, the stop extends from one of the legs 12, 14 or 16 and is oriented so that it is interposed between two adjacent legs and limits relative movement of those adjacent legs when the stop abuts the adjacent leg. Preferably the stop comprises an enlarged portion on the post 40 which is sized so that it does not fit through the hole 44, either because it is too large or because the shape prevents passage through the hole. Preferably the stop takes the form of a larger diameter base 46 on the post 40, with the tapered end 42 extending from the end of base 46. Thus, as the tapered end 42 enters hole 40, the base 46 abuts the leg 12 or 14 adjacent the hole 40 and limits motion of the legs 12, 14 relative to middle leg 16. Because the entrance of the tapered end 42 into the hole 44 also restrains lateral motion of the middle leg 16 relative to the outer legs 12, 14, it also may be considered a portion of the motion limiting mechanism to the extent of the desired limitation of lateral motion.

The motion limiting portion of mechanism 20 can be used separately from the alignment portion. Thus, the motion limiting portion could comprise a post or stop extending from the middle leg 16 and abutting one of the adjacent legs to limit relative motion of the legs. The stop, such as post 40, could also extend from one or both of the outer legs 12, 14 toward the middle leg 16. There is thus provided a motion limiting means for limiting the motion of one or both of the outer legs 12, 14 relative to the middle leg 16, in the lateral plane of the legs 12, 14, 16 and also in the plane of the longitudinal axes of the legs 12, 14 and 16.

Referring to FIGS. 1–2 it can be seen that, the distance at which the enlarged base 46 abuts and stops the movement of the outer leg 12 or 14, affects the latching mechanism 18. Advantageously, the enlarged base 46 abuts the outer leg 12 shortly before the latching members 32 enter the space formed by the offset that separates the members 32 from the legs 12, 14. The outer leg 12 is flexible enough that the offset latching members 32 can be engaged by pressing on outer leg 12, after the enlarged base 46 abuts the outer leg 12.

The stop, such as the enlarged base 46 of post 40, also serves as a pivot mechanism. If the outer legs 12, 14 are moved toward middle leg 16 by pressing on the outer legs 12, 14, then the enlarged base portion 40 will be interposed between middle leg 16 and the outer legs 12, 14. Depending on where the surgeon is pressing the outer legs 12, 14 of the triceps 10 relative to the stop, this can open or close the distal ends 22, 24 of the triceps. If the operator's fingers are pressing the outer leg 12 between the location of the hole 44 (and aligned base 46) and the latching mechanism 18, in addition to pressing the outer leg 14 between the location of the hole 44 and the joined end 11, then when the outer legs 12, 14 hit the stop, such as base 46, they will bend or pivot about the base 46, causing the distal ends 22, 24 to move away from the distal end 26 of the middle leg 16.

Conversely, by pressing on the outer legs 12, 14 between the location of the holes 44 and the distal ends 22, 24, the distal ends 22, 24 will move toward the middle leg 16. Whether by material selection or shaping the legs, the outer legs 12, 14 are configured so that they can bend when pressed by a surgeons' fingers to pivot about the stop to open the space between the distal ends 22, 24, 26. Thus, there is provided a means for opening and closing the triceps 10 by moving the distal ends 22, 24 relative to the distal end 26 of the middle leg 16.

Finally, if the surgeon repositions his or her fingers to press on outer leg 12 between the latching mechanism 18 and the joined end 11, the leg 12 and its distal end 22 will move toward the middle leg 16 until the latching mechanism 18 is either engaged or until latching members 32 abut. Thereafter further pressing at the same location will cause outer leg 12 to pivot about the post base 46 and move distal end 22 away from distal end 26. There is thus provided means for moving the distal ends 22, 26 relative to each other.

The legs 12, 14, 16 are preferably elongated, flat strips of metal. The width, thickness and other dimensions will vary with the type of tissue that is being manipulated by the triceps. The legs must, however, be wide enough to facilitate gripping by the surgeon's fingers at the middle, and preferably taper to a narrow, distal end 22, 24, 26. Advantageously, a surgical steel is used which can be sterilized in an autoclave for reuse, although other materials can be used, including plastics, as long as they are compatible for use in anastomosis.

The distal ends 22, 24 and 26 have tips configured for anastomosis. Furthermore, at least one of the tips is preferably colored so that the colored tip, and the orientation of the triceps 10, can be determined when viewing the triceps through optical instruments. Plating one tip with a biologically compatible, but different colored material, preferably a metal, can achieve this purpose.

Figure 5:
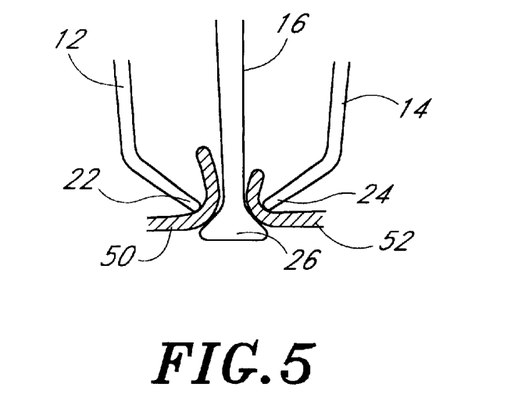
FIG. 5 is an plan view of a first embodiment of the distal ends of the triceps of FIG. 1 in use to join two vessel walls.

Referring to FIG. 5, the distal end 26 of the middle leg 16 has an inclined surface that extends away from a longitudinal axis of the middle leg 16 at an obtuse angle, with the distal ends 22, 24 of the outer legs 12, 14, respectively, being located to press a vessel wall against the inclined surface when in use. Advantageously, the distal extremity of end 26 of the middle leg 16 has a triangular cross section, or preferably a conical shape with the wide portion of the cone or triangle at the distal end and the tip of the cone or triangular section joined to the end of the straight, middle leg 16 to help urge tissue up against the leg and to gently prevent the tissue from sliding off the middle leg 16. However, the flange 64 on distal end 24 impedes disengagement of the distal end 24 of the triceps after the tissue is joined. Thus, in an alternative embodiment, the triceps 10 has a middle leg 26 with a cylindrical distal end 26.

Figure 9:
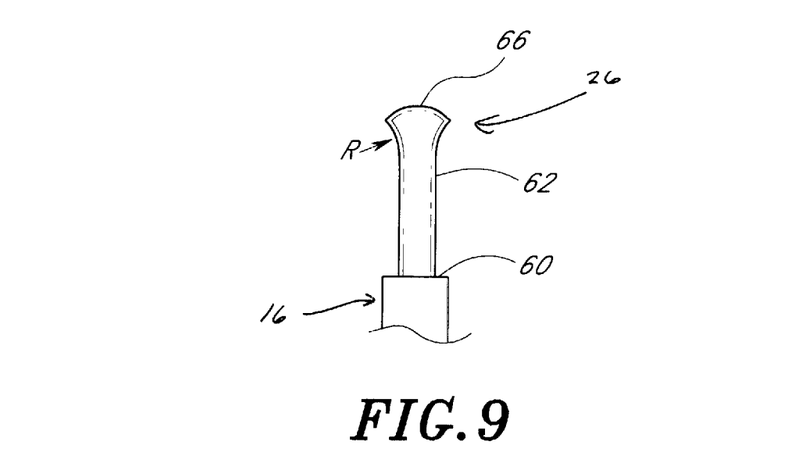
FIG. 9 is a plan view of an alternate embodiment of a distal end of the middle leg of the triceps of FIG. 1.

In a still further embodiment, shown in FIG. 9, the distal end 26 of middle leg 16 has an enlarged end, but a gentle radius R about twice the diameter of the distal end 26 leads up to said distal end. The enlarged head allows a protruding surface that helps avoid the engaged tissue from slipping off the end 26, while the radius allows easy removal when the tissue is sutured.

The distal ends 22, 24 of the outer legs 12, 14 advantageously are angled toward the middle leg 16, and have a concave shape that conforms to the shape of distal end 26, although a straight end could also be used—especially if the end 26 is triangular in cross-section. By positioning the end 26 in a vessel lumen and resiliently urging the distal ends 22, 24 of the outer legs 12, 14 toward the distal end 26, the vessel wall 50 can be held between the outer distal end 22 and middle distal end 26, while a different vessel wall 52 can be held by outer distal end 24 and middle distal end 26. By opening and closing outer legs 12, 14 separately or together, as discussed above, the vessel walls 50, 52 can be positioned and held for joining.

Typically, vessel wall 50 is gripped first between outer distal end 22 and middle distal end 26, causing the vessel to partially evert. The latching mechanism 18 may be engaged to make it easier for the surgeon to handle the triceps 10. The middle distal end 26 is then inserted into the lumen vessel 52 with the outer distal end 24 on the outside of the vessel 52. While controlling movement of the outer leg 14 of triceps 10 with the fingers, the surgeon can grip the vessel 52 and partially evert it while holding the edges of vessels 50, 52 in position for convenient application of a clip or connector to join the vessels 50, 52. Once a first suture, staple or clip is applied, the eversion remains stable and the triceps 10 can be withdrawn by releasing the vessel walls 50, 52.

Figure 6:
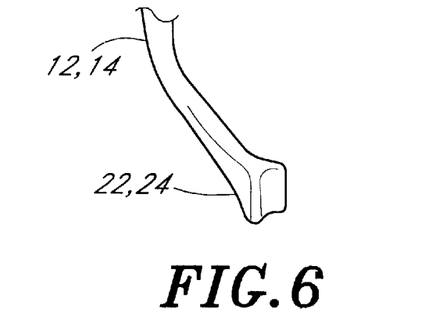
FIG. 6 is an perspective view of a second embodiment of the distal end of an outer leg of the triceps of FIG. 1.
Figure 7:
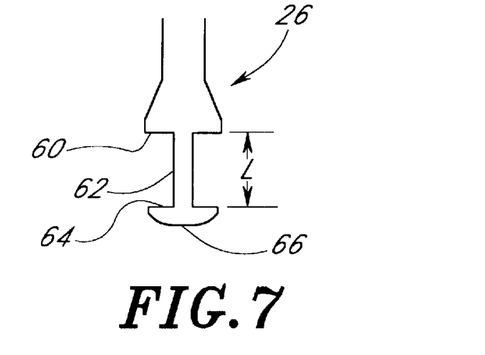
FIG. 7 is an plan view of a second embodiment of the distal end of the middle leg of triceps of FIG. 1.
Figure 8:
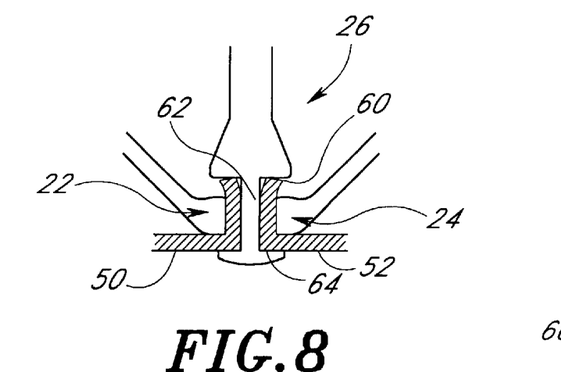
FIG. 8 is an plan view of the second embodiment of the distal ends of the triceps of FIGS. 6–7 in use to join two vessel walls.

A further embodiment of the distal ends 22, 24, 26 is shown in FIGS. 6–8. The middle distal end 26 has an outwardly extending surface or flange 60. Extending from the center of the flange 60 and along the longitudinal axis of middle leg 26, is an engaging surface 62. The surface 62 can have diverse shapes, but preferably has a circular cross-section, or an elliptical cross-section with the major axis of the ellipse extending through the distal ends 22, 24.

Referring to FIGS. 6 and 8, the distal ends 22, 24 are preferably shaped to conform to the engaging surface 62, and thus have concave surfaces. If the engaging surface 62 is cylindrical, then distal ends 22, 24 have a concave, preferably cylindrical recess aligned to engage the cylindrical engaging surface 62 when a vessel wall 50, 52 is interposed between engaging surface 62 and distal ends 22, 24 (FIG. 8). The shape of engaging surface 62 and distal ends 22, 24 is selected to help evert the vessel walls 50, 52. There is thus advantageously provided means on the distal ends 22, 24, 26 for holding and everting tubular vessels for anastomosis.

Figure 10:
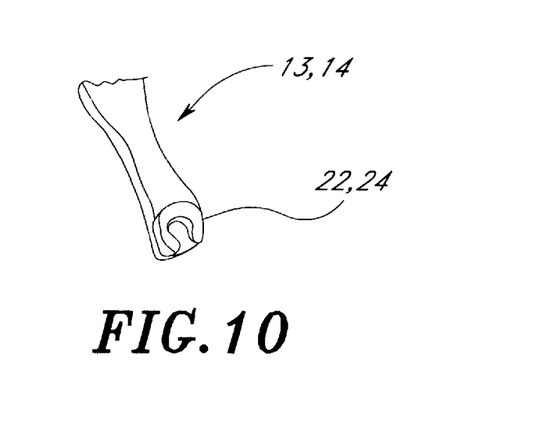
FIG. 10 is a perspective view of an alternate embodiment of a distal end of the outer legs of the triceps of FIG. 1.

In a further embodiment shown in FIG. 10, the engaging surfaces 22, 24 on outer legs 12, 14 advantageously have a convexly curved surface. The curved surface is advantageously a portion of a circle, but is preferably shaped like a horseshoe so that engaged tissue abuts the contour of the horseshoe and is pressed into the center of the horseshoe by the middle distal end 26. This configuration increases the contact area between the ends 22, 24, 26 and the engaged tissue, helping to reduce crushing of the tissue, while also increasing the eversion of the tissue and increasing the ease of gripping and manipulating the tissue. The center portion of the horseshoe shape cannot be recessed greatly, as this may allow the middle distal end 26 to act like a scissors to cut the engaged tissue. The workable dimensions will vary with the type of tissue being manipulated by the triceps 10.

In a further embodiment, at the distal end of the engaging surface 62 is another outwardly extending surface or flange 64 that is parallel to the flange 60. Opposite the flange 64 is a facing flange 66 with a distal surface that is advantageously convexly curved in order to avoid damage to body tissue during use. The flanges 60, 64 preferably extend completely around the engaging surface 62. Flange 60 extends from the engaging surface 62 a distance sufficient to hold vessel walls 50, 52 or other engaged tissue from moving past the flange 60. The distance needed for the flange will vary with the type of tissue being manipulated by the triceps 10. The flange 64 extends a distance similar to that of flange 60 in order to help evert the tubular vessel, but flange 64 could be shorter than flange 60. The flanges 60, 64 are spaced apart a distance L sufficient to accommodate the jaws formed on outer distal ends 22, 24, and the tissue being joined, as reflected in FIG. 8.

The distal ends 22, 24 can also be generally flat ends, tapered at about 45° so the ends can abut along the longitudinal length of the distal end 26 of middle leg 16. In this alternative embodiment, the distal ends 22, 24 have slightly rounded corners in order to break sharp corners and edges that might otherwise cut the engaged tissue. The precise dimensions of the distal ends 22, 24, 26 will vary with the tissue being engaged, with smaller dimensions being generally preferred for smaller vessels or pieces of tissue, and larger dimensions being used for larger vessels or pieces of tissue. If the dimensions are too small for the size of the tissue, then the force applied on the distal ends 22, 24, 26 increases enough that it pokes through or into the engaged tissue, or otherwise cuts the tissue.

In more general terms, the distal end 26 of the middle leg 16 has a convexly curved engaging portion 62 extending for a first predetermined length (L) along the longitudinal axis of the middle leg 16. The distal ends 22, 24 of each outer leg 12, 14 also have a concavely curved surface extending for a second predetermined length along a longitudinal axis of each leg, where the first predetermined length (L) is greater than the second predetermined length. The predetermined lengths are located so that the inwardly curved shapes urge a vessel wall 50 or 52, against the outwardly curved shape 62 during use.

Referring to FIGS. 5 and 8, the flange 60 (FIG. 8) helps limit movement of the vessel walls 50, 52 along the longitudinal axis of middle leg 16 and to align the edges of the tissue to be joined in order to provide for a symmetric eversion which makes it easier to clip the vessel walls together. This contrasts with the conical distal end 26 shown in FIG. 5, which does not limit motion of the vessel walls 50, 52, and which does not align the edges of the tissue, and which can result in unevenly matched tissue that are more difficult to fasten together by clips or other means. There is thus provided means for limiting the movement of the tissue to be joined and for aligning the tissue for joinder.

In more general terms, the distal end 26 of the middle leg 16 has an outwardly extending flange 60 at the end of the convex surface 62 and inward (toward the joined ends 11) of a location at which the distal ends 22, 24 of the outer legs 12, 14 would urge vessel walls 50, 52 against the middle leg 16 when in use. The flange 60 advantageously extends a distance sufficient to act as a motion stop for the vessel walls 50, 52 that are urged against the convex surface 62 of the middle leg 16 by the distal ends 22, 24 of the outer legs 12, 14.

The triceps 10 of this invention offers several advantages. By pressing the outer legs 12, 14 toward each other the surgeon can engage tissue 50, 52 for anastomosis between the distal ends of the middle leg 16 and an outer leg (12 or 14). By removably latching the outer leg 12 or 14 relative to the middle leg 16 and in a position to hold the engaged tissue 50, 52 (FIG. 8), the surgeon can make it easier to manipulate the triceps 10 because the latch mechanism 18 relieves the surgeon of applying the correct pressure and avoids accidentally disengaging the tissue from the triceps. Advantageously the latching is achieved by moving at least one of the middle 16 and the outer leg, e.g., outer leg 12, relative to the other leg to engage adjoining surfaces, with further movement in the same direction disengaging the latch.

A further advantage is offered by interposing a stop, such as enlarged base 46, intermediate the middle leg 16 and one or both of the outer legs 12, 14 to limit the motion of the distal ends 22, 24 of the outer legs and to prevent gripping the tissue 52 (FIG. 8) too tightly so as to cause a scissors effect that cuts the tissue being gripped. Once the stop 46 is engaged with the opposing leg, additional pressure on the outer leg 14 between the joined ends 11 and the post 40 will cause the outer leg 14 to pivot about the base 46 and open or increase the distance between the middle distal end 26 and the outer distal end 24, thus loosening the grip on the tissue. This loosening avoids scissoring and cutting the tissue. It also allows adjustments of the grip on the tissue. Further, when the stop 46 engages the outer leg 14, then if desired, the grip can be tightened by placing additional pressure on the outer leg 14 between the stop 46 and the distal end 24 the grip on the tissue 52 (FIG. 8).

A similar advantage arises by interposing the stop 46 intermediate the latch mechanism 18 and the distal end 22. The middle and outer legs 12, 16 can be moved toward each other until the stop 46 limits the motion. Advantageously, the relative motion is stopped at a point where the distal end 22, 26 of the middle and outer legs 12, 16 have gripped the tissue 50 (FIG. 8) for anastomosis, and the latch mechanism 18 is engaged to hold the engaged tissue in place. But, if needed, the grip on that engaged tissue 52 can be adjusted by opening and closing the distance between the distal ends 22, 26 of the middle and outer legs 12, 16 by pressing between the latch mechanism 18 and the stop 46, which causes the outer leg to pivot about the stop 46 and loosen the grip on the engaged tissue 50 (FIG. 8). The opening of the ends 22, 26 with additional pressure also avoids the undesirable scissoring and cutting of the gripped tissue.

While the above is described regarding an anastomosis for a tubular vessel, the term anastomosis is used broadly herein to refer to joining tubular vessels, skin closures or joining other tissues. Depending on the nature of the tissue to be held and joined by the triceps 10, the size and shape of the legs 12, 14, 16, and the size and shape of the distal ends 22, 24 and 26, may be varied as needed. Further, the triceps 10 has been described with an advantageous combination of features that include a latch mechanism 18, stops 40, alignment mechanism 20, and distal ends 22, 24, 26 advantageously configured for anastomosis. Each of these features may be used separately, or in various combinations with the other features.

While the triceps of the present invention has been described with a certain degree of particularity, it is manifest that many changes may be made in the specific designs, constructions and methodology hereinabove described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

What is claimed is:

1. A surgical triceps having three legs fastened at one end and including two outer legs on opposing sides of a middle leg, the outer legs being configured to be separated from the middle leg and resiliently urgable toward the middle leg by finger pressure, each leg having a free distal end that is separated from the adjacent distal ends but which may be resiliently urged toward each other by finger pressure, the distal ends being configured for anastomosis, so that first and second pieces of tissue can be urged by the distal ends of the outer legs against the distal end of the middle leg with sufficient force to hold the tissue for joining, comprising:

a Castro Viejho latch on at least one of the legs engaging a portion of an adjacent leg to hold the adjacent legs in position, the latch being configured to achieve a predetermined spacing at the distal ends of the adjacent legs such that the distal end of the one outer leg and the distal end of the middle leg approximate each other sufficient to hold tissue for joining when in use but are spaced apart a predetermined distance.

2. A triceps as defined in claim 1 further comprising an alignment member extending from one of the middle or one of the outer legs and aligned to engage a recess in the middle or the other of the outer legs to ensure alignment of the distal ends of the middle leg and an adjacent distal end on one of the legs when the member engages the recess.

3. A triceps as defined in claim 2 further comprising a stop extending from one of the legs and orientated so that the stop is interposed between two adjacent legs to contact and limit motion between said adjacent legs upon contact.

4. A triceps as defined in claim 3, wherein the stop and alignment members are coaxially located on a common member.

5. A triceps as defined in claim 1, wherein the distal end of the middle leg has a flange extending outwardly from the middle leg and spaced from the distal end and toward the fastened ends a distance sufficient to contact the tissue being gripped by adjacent legs to align the tissue for symmetric eversion during use of the triceps, the flange extending from the middle leg a distance sufficient to block passage of tissue to be joined by anastomosis during use of the triceps.

6. A finger operated surgical triceps for anastomosis, comprising three legs fastened at one end and having distal ends configured for anastomosis, the legs including a middle leg interposed between a first and second outer legs, each of the outer legs being adjacent the middle leg but on opposing sides thereof, and a stop interposed between the middle leg and at least one of the adjacent outer legs to limit motion of the at least one adjacent, outer leg toward the middle leg, the at least one outer leg being movable for a distance before engaging the interposed stop.

7. A method for anastomosis using finger operated triceps having three legs fastened at one end and having distal ends configured for anastomosis, the legs including a middle leg interposed between a first and second outer legs, comprising the steps of:

manually moving the first leg toward the middle leg and engaging tissue for anastomosis between the distal ends of the middle leg and the first leg;

engaging a stop interposed between the first and middle legs which limits how close the first and middle legs can come to one another, and removably latching the first outer leg and middle leg in a position to hold the engaged tissue.

8. A method as defined in claim 7, comprising the further step of manually moving the second leg toward the middle leg and engaging tissue for anastomosis between the distal ends of the middle leg and the second leg.

9. A method as defined in claim 8, comprising the further step of urging an end of the tissue engaged between the first and middle legs and between the second and middle legs against an outwardly extending flange on the middle leg to align the ends of the tissue with the flange.

10. A method as defined in claim 7, wherein the latching step comprises the step of using a Castro Viejho latch.

11. A method as defined in claim 7, wherein the latching step is achieved by a latch that limits the movement of the first leg toward the middle leg, and wherein a stop is interposed intermediate the middle and first outer legs and located between the latch and the distal end of the first outer leg, and comprising the further step of moving the middle and first outer legs toward each other until the stop limits the motion of the middle and first outer legs, and then opening the distance between the distal ends of the middle and first outer legs by pressing on the first outer leg intermediate the stop and the latch.

12. A method as defined in claim 7, comprising the further steps of urging tissue by horseshoe shaped, concave, distal ends of the outer members toward a convex distal end of the middle member to evert the tissue for anastomosis.

13. A finger operated surgical triceps for anastomosis, comprising three legs fastened at one end and having distal ends configured for anastomosis, the legs including a middle leg interposed between a first and second outer legs, each of the outer legs being adjacent the middle leg but on opposing sides thereof, and a stop interposed between the middle leg and each of the outer legs to limit motion of the outer legs toward the middle leg, the outer legs being movable for a distance before engaging the interposed stop.

14. A finger operated surgical triceps for anastomosis, comprising three legs fastened at one end and having distal ends configured for anastomosis, the legs including a middle leg interposed between a first and second outer legs, each of the outer legs being adjacent the middle leg but on opposing sides thereof, a stop interposed between the middle leg and at least one of the adjacent outer legs to limit motion of the at least one adjacent, outer leg toward the middle leg, the at least one outer leg being movable for a distance before engaging the interposed stop, and an alignment member coaxially aligned with the stop and configured to engage a recess in one of the adjacent legs to restrain lateral movement of two of the legs.

15. A finger operated surgical triceps for anastomosis, comprising three legs fastened at one end and having distal ends configured for anastomosis, the legs including a middle leg interposed between a first and second outer legs, each of the outer legs being adjacent the middle leg but on opposing sides thereof, a stop interposed between the middle leg and at least one of the adjacent outer legs to limit motion of the at least one adjacent, outer leg toward the middle leg, the at least one outer leg being movable for a distance before engaging the interposed stop, and a latch mechanism located between the middle leg and one of the outer legs and further being located between the fastened end of the legs and the stop interposed between the middle leg and one of the outer legs, the latch engaging one of the middle or said outer leg to limit motion of said outer leg away from the middle leg, the latch being configured so the distance between the distal ends of the middle leg and the at least one of the outer legs is at a predetermined distance sufficient to grip tissue for anastomosis.

16. A finger operated surgical triceps for anastomosis, comprising three legs fastened at one end and having distal ends configured for anastomosis, the legs including a middle leg interposed between a first and second outer legs, each of the outer legs being adjacent the middle leg but on opposing sides thereof and a stop interposed between the middle leg and at least one of the adjacent outer legs to limit motion of the at least one adjacent, outer leg toward the middle leg, the at least one outer leg being movable for a distance before engaging the interposed stop, and the outer legs have a concave portion at their distal ends that is located to coincide with a smaller sized portion on the distal end of the middle leg to help evert tissue gripped between the distal end of the middle leg and one of the distal ends on the outer legs.

* * * * *